US00PP21238P2

(12) United States Plant Patent
Madsen

(10) Patent No.: US PP21,238 P2
(45) Date of Patent: Aug. 24, 2010

(54) ***RHIPSALIDOPSIS* PLANT NAMED '7304G'**

(50) Latin Name: *Rhipsalidopsis×hybrida*
Varietal Denomination: 7304G

(75) Inventor: Christian Hald Madsen, Korsor (DK)

(73) Assignee: Gartneriet PKM A/S, Odense (DK)

( * ) Notice: Subject to any disclaimer, the term of this patent is extended or adjusted under 35 U.S.C. 154(b) by 0 days.

(21) Appl. No.: 12/378,825

(22) Filed: Feb. 22, 2009

(51) Int. Cl.
*A01H 5/00* (2006.01)

(52) U.S. Cl. ..... Plt./372

(58) Field of Classification Search ..... Plt./372
See application file for complete search history.

(56) References Cited

OTHER PUBLICATIONS

Upov-rom GTITM, Plant Variety Database GTI Jouve Retrieval Software, Citation for '7304G', one page.*
Print-out of application number and filing date from Community Plant Variety Office (CPVO) website for corresponding, CPVO application No. 2007/1169 filed May 25, 2007. (http://www.cpvoextranet.cpvo.europa.eu).

* cited by examiner

*Primary Examiner*—June Hwu
(74) *Attorney, Agent, or Firm*—Foley & Lardner LLP

(57) ABSTRACT

A new and distinct *Rhipsalidopsis* plant named '7304G' particularly characterized by its large upright to vertical flowers which are red-purple in color; large quantity of flowers per plant; freely branching growth habit; and ovoid to lanceolatoid in shape buds.

4 Drawing Sheets

Latin name of the genus and species of the plant claimed: *Rhipsalidopsis×hybrida.*

Variety denomination: '7304G'.

BACKGROUND OF THE INVENTION

The present invention relates to a new and distinct cultivar of *Rhipsalidopsis* plant, botanically known as *Rhipsalidopsis×hybrida* sometimes referred to as *Rhipsalidopsis* Britton Et Rose, including *Epiphylopsis* Berger, commonly known as either Easter Cactus or Spring Cactus, and hereinafter referred to by the cultivar name '7304G'.

The new *Rhipsalidopsis* cultivar is a product of a controlled breeding program conducted by the inventor, Christian Hald Madsen, in Søhus, Denmark. The objective of the breeding program was to develop a new *Rhipsalidopsis* cultivar with compact, freely branching habit and unique colored flowers.

The new *Rhipsalidopsis* cultivar originated from a cross made by the inventor in 2002 in Søhus, Denmark. The female or seed parent is the *Rhipsalidopsis×hybrida* cultivar designated 'PKMØ1' (unpatented). The male or pollen parent is the *Rhipsalidopsis×hybrida* cultivar designated 'PKMINA' (unpatented). The new *Rhipsalidopsis* cultivar was discovered and selected by the inventor as a single flowering plant within the progeny of the stated cross in a controlled environment in 2007 in Søhus, Denmark. The inventor selected '7304G' on the basis of its flower color, upright, plant habit and freely branching habit.

Asexual reproduction of the new *Rhipsalidopsis* cultivar by phylloclade cuttings was first performed in May of 2007 in Søhus, Denmark, and has demonstrated that the combination of characteristics as herein disclosed for the new cultivar are firmly fixed and retained through successive generations of asexual reproduction. The new cultivar reproduces true to type.

BRIEF DESCRIPTION OF THE INVENTION

The following traits have been repeatedly observed and are determined to be unique characteristics of '7304G' which in combination distinguish this *Rhipsalidopsis* as a new and distinct cultivar:

1. Large upright to vertical flowers which are red-purple in color;
2. Large quantity of flowers per plant;
3. Freely branching growth habit; and
4. Ovoid to lanceolatoid in shape buds.

Plants of the instant cultivar '7304G' differ primarily from plants of the parental cultivars 'PKMØ1' (female or seed parent) and 'PKMINA' (male or pollen parent) by the following characteristics:

1. Plants of '7304G' are shorter than plants of the parental cultivars.
2. Plants of '7304G' have more lateral branches (when 3 phylloclade cuttings planted per plant) than the plants of the parental cultivars.
3. Plants of '7304G' have more flowers than plants of the parental cultivars.
4. Plants of '7304G' have red-purple flowers (RHS N74B) whereas the parental cultivars have red-purple colored flowers (RHS N74D) 'PKMØ1' (female or seed parent) and red-purple colored flowers (RHS 71B) 'PKMINA' (male or pollen parent).

Side-by-side comparisons were conducted by the inventor in Søhus, Denmark, among plants of the instant cultivar '7304G' and plants of the most similar commercial cultivar, *Rhipsalidopsis* ANDROMEDA® (patented, Denmark Grant No. 13274, granted Sep. 12, 1989; and Netherlands Grant No.: 9812, granted Dec. 27, 1989). Plants of the new *Rhipsalidopsis* '7304G' differ from plants of *Rhipsalidopsis* ANDROMEDA®, primarily in the following characteristic:

1. Plants of '7304G' are taller (about 16 cm) than plants of the *Rhipsalidopsis* ANDROMEDA® (about 14 cm).

2. Plants of '7304G' produce more flowers and buds per plant (about 30 to 45) than plants of *Rhipsalidopsis* ANDROMEDA® (about 25 to 30).
3. Plants of '7304G' produce red-purple flowers (RHS N74C when fully opened) whereas plants of *Rhipsalidopsis* ANDROMEDA® have red-purple flowers (RHS 73A when fully opened).
4. Plants of '7304G' produce darker yellow-green mature phyllocades (RHS 147A) than plants of than plants of the *Rhipsalidopsis* ANDROMEDA® (RHS 146A).
5. Plants of '7304G' produce larger phylloclades (about 3-4 cm in length and 20-33 mm in width) than plants of than plants of the *Rhipsalidopsis* ANDROMEDA® (about 2-3 cm in length and 15-25 mm in width).

BRIEF DESCRIPTION OF THE PHOTOGRAPHS

The accompanying photographs illustrate the overall appearance of the new *Rhipsalidopsis* cultivar '7304G' showing the colors as true as is reasonably possible with colored reproductions of this type. Colors in the photographs may differ slightly from the color values cited in the detailed botanical description, which accurately describe the color of '7304G'.

DETAILED BOTANICAL DESCRIPTION

Figure 1:
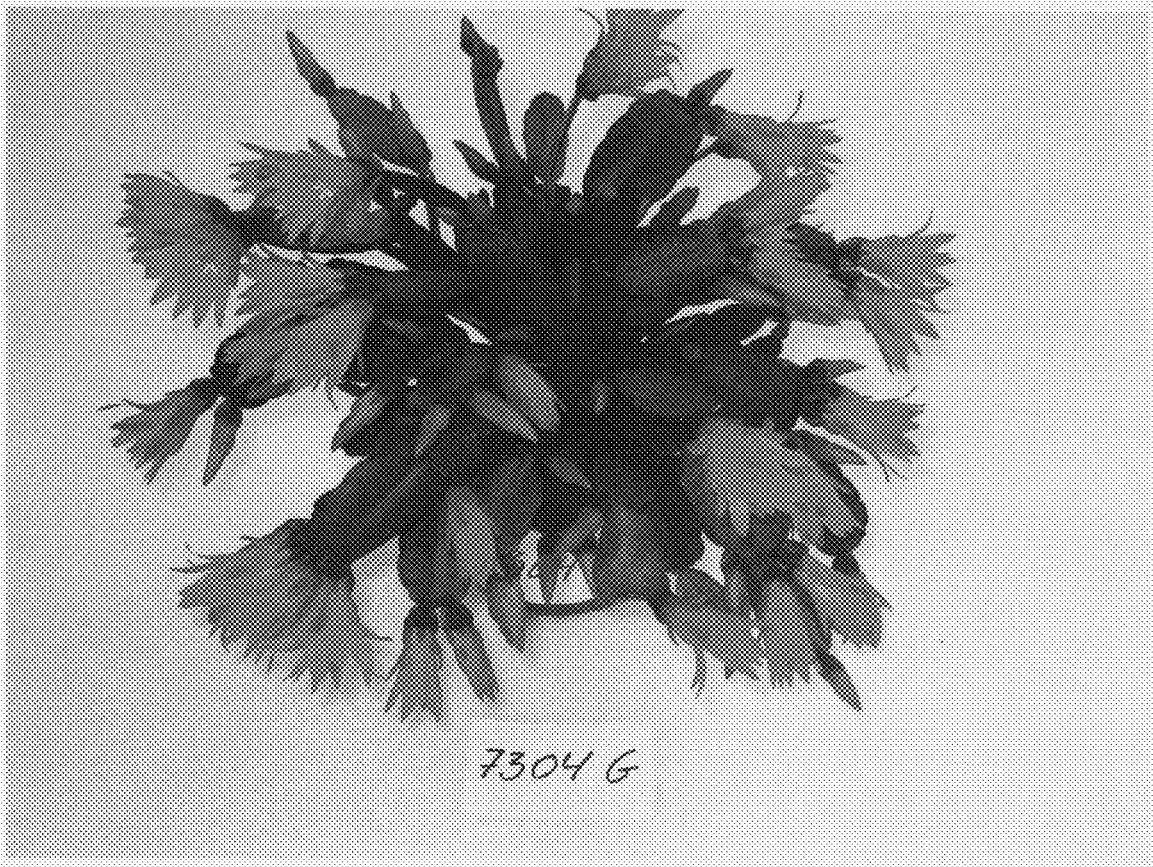
FIG. 1 shows a side perspective view of a typical flowering plant of '7304G' grown in a 9.0 cm pots, at 9 months of age.
Figure 2:
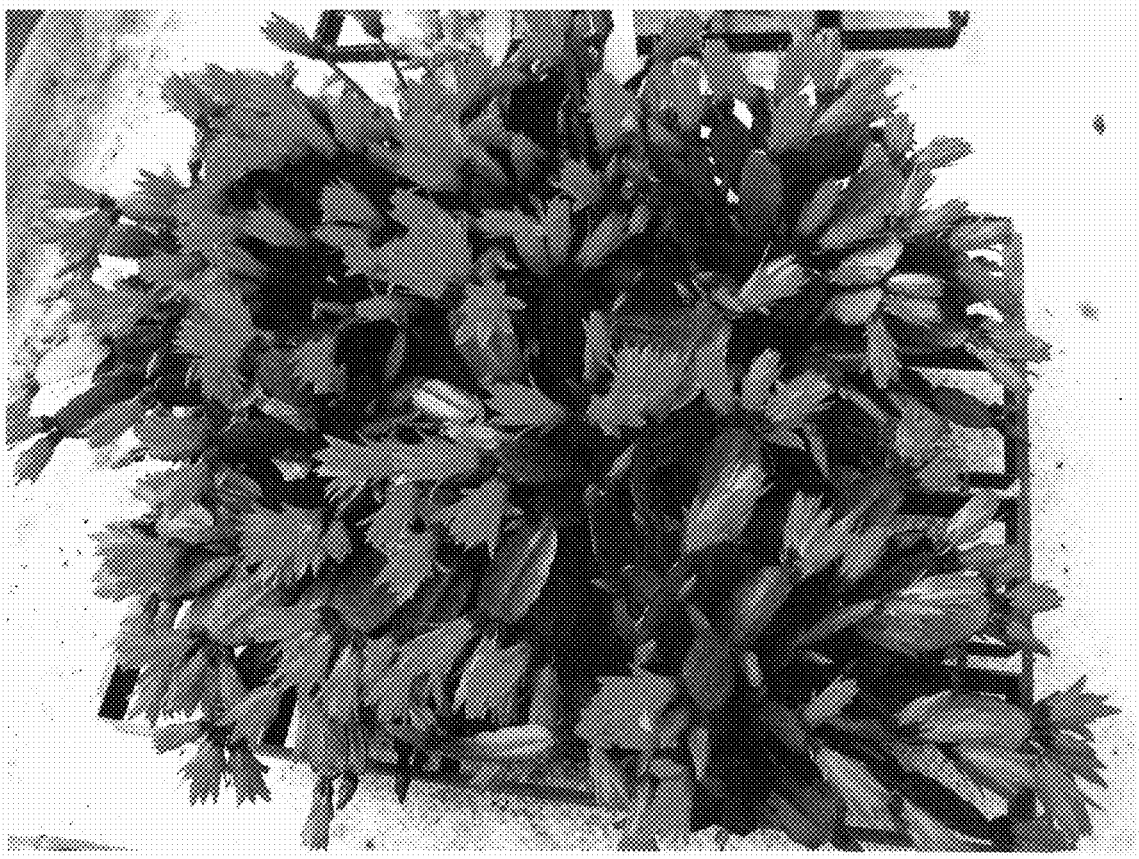
FIG. 2 shows a top perspective view of a typical flowering plants of '7304G' grown in a 9.0 cm pots, at 9 months of age.
Figure 3:
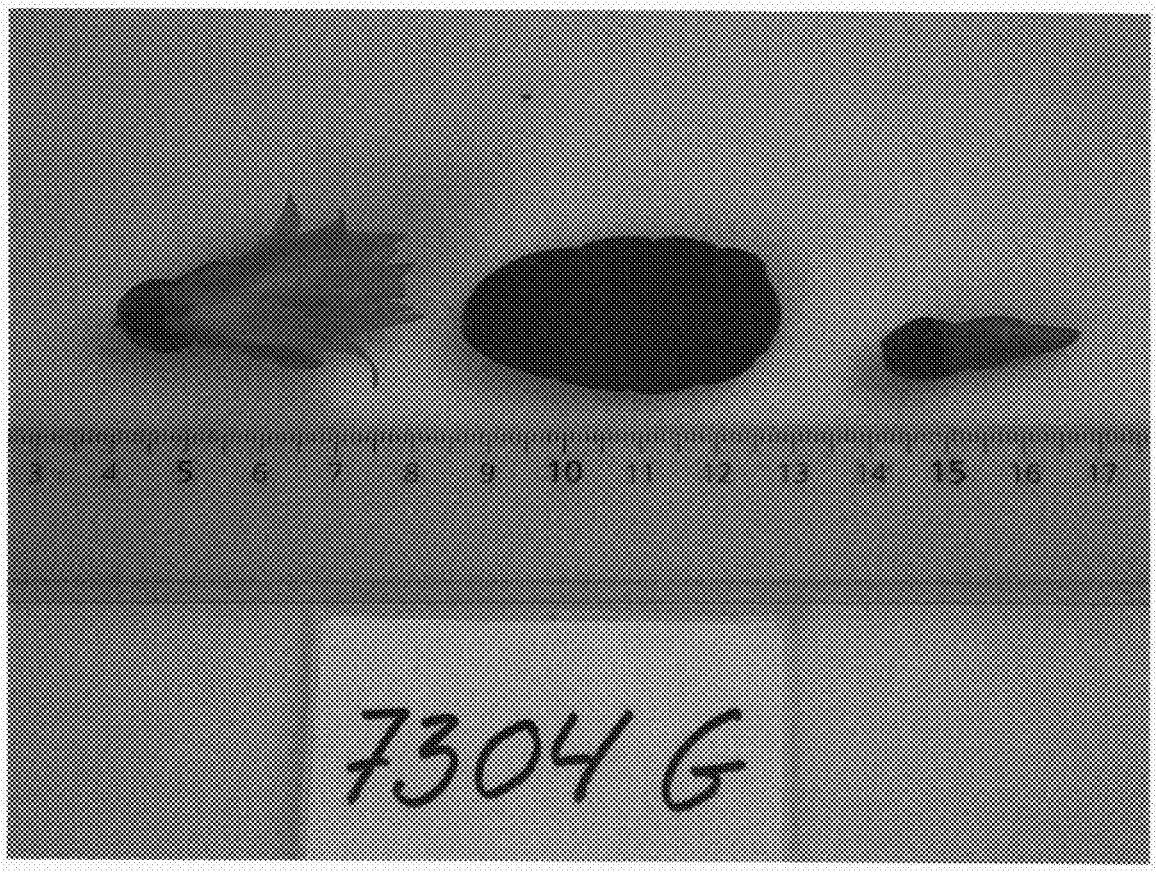
FIG. 3 shows a close-up perspective view of a typical mature flower, phylloclade, and bud produced by '7304G' at 9 months of age.
Figure 4:
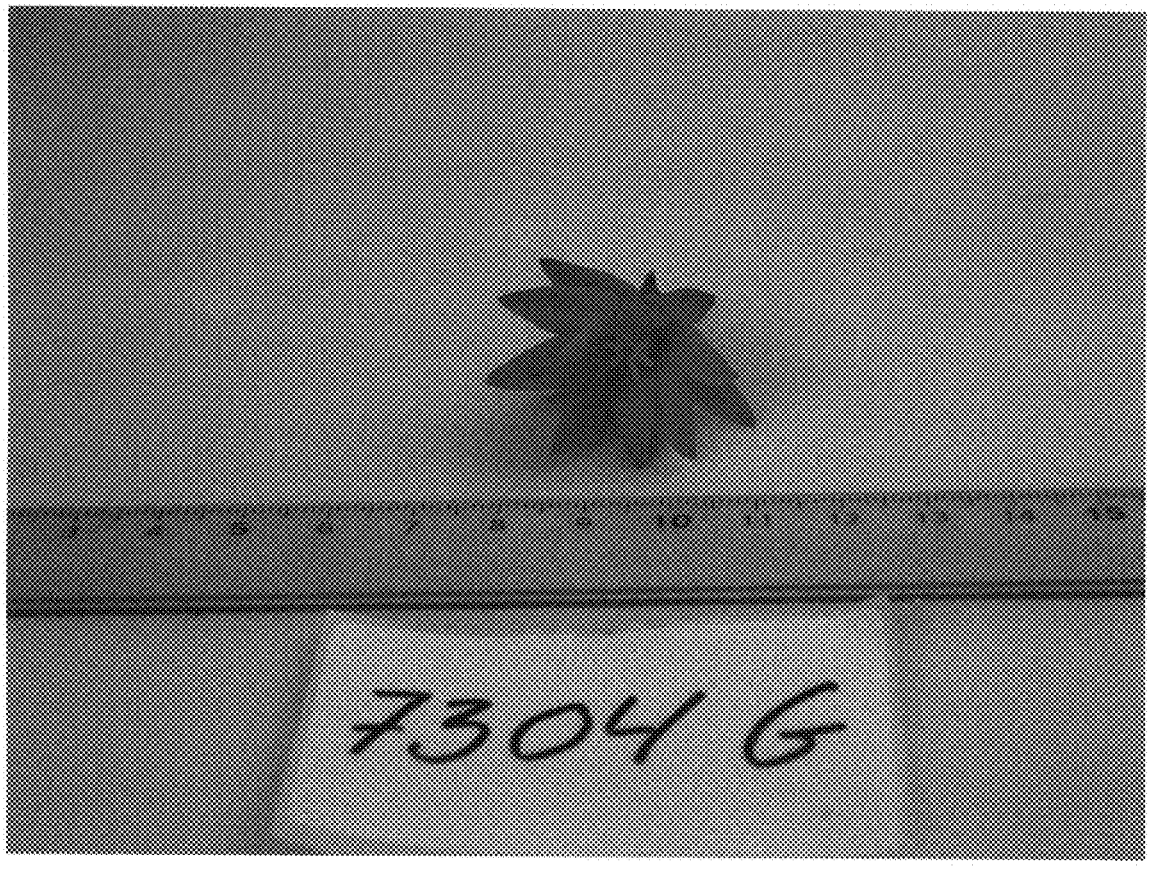
FIG. 4 shows a close-up top perspective view of a typical mature flower produced by '7304G' at 9 months of age.

The new *Rhipsalidopsis* cultivar '7304G' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe plants of '7304G' as grown in a glass-covered greenhouse in Fyn, Denmark, under conditions which closely approximate those generally used in commercial practice, where day temperatures in the greenhouse average 18° C. and night temperatures in the greenhouse average 16° C. Ambient light levels used while growing plants of '7304G' are +50Wm$^2$. Plants of '7304G' are themo-photoperiodic and will develop buds and bloom best under short day treatment in 6-8 weeks and cool day/night temperatures of about 8°. No growth retardants were used when growing plants of '7304G'.

The age of the '7304G' plants described is 9 months old and grown in 9.0 cm pots. The photographs and descriptions were taken during the winter season. Color references are made to The Royal Horticultural Society Colour Chart (R.H.S.), 4$^{th}$ edition, except where general colors of ordinary significance are used.

Classification:

*Botanical.*—*Rhipsalidopsis* Britton Et Rose.

*Common name.*—Easter Cactus or Spring Cactus.

Parentage:

*Female or seed parent.*—*Rhipsalidopsis* Britton Et Rose designated 'PKMØ1' (unpatented).

*Male or pollen parent.*—*Rhipsalidopsis* Britton Et Rose designated 'PKMINA' (unpatented).

Propagation: By phylloclade cuttings.

*Time and temperature to initiate roots.*—In a greenhouse, about 16 days at 18° C. to 21° C.

*Time and temperature to produce a young plants.*—In a greenhouse, about 60 days at at 18° C. to 21° C.

*Rooting habit and description.*—Fine, well-branched and yellow-white, RHS 158A in color.

Plant:

*Type.*—Perennial, Epiphyte.

*Growth habit.*—Initially erect and upright, becoming pendent as lateral branches lengthen.

*Branching habit.*—Freely branching, with two or there new phylloclades forming at the apical end of older phylloclades.

*Vigor.*—Slow growth rate.

*Crop time.*—After rooting, about 9 months are required to produce a finished flowering plant in an 9 cm pot.

*Size at maturity.*—Height (soil level to top of plant, including flowers): About 16 cm. Spread: About 20 cm to 22 cm.

Stem: None, older phylloclades may turn woody with age (several years).

Lateral branches:

*Arrangement.*—Phylloclades form at the apex of older phylloclades to form branches.

*Quantity.*—About 9 to 12, when 3 phylloclade cuttings planted per pot.

*Length.*—Primary: About 3 cm to 4 cm (1 phylloclade). Secondary: About 12 cm (3 or 4 phylloclades).

*Width.*—About 2 cm to 3 cm.

*Aspect.*—Upright to arching (from basal phylloclade).

*Strength.*—Strong (from basal phylloclade).

*Appearance.*—Dull/matte.

*Pubescence.*—None.

Phylloclade:

*Arrangement.*—Single and sequential.

*Length.*—About 3 cm to 4 cm.

*Width.*—About 2 cm to 3 cm.

*Thickness.*—About 4 mm to 6 mm (at center vein of phylloclade).

*Overall shape.*—Oval.

*Apex shape.*—Truncate.

*Base shape.*—Rounded.

*Margin.*—Crenate.

*Texture.*—Glabrous, smooth.

*Pubescence.*—None.

*Color of immature phylloclade.*—Upper and lower surfaces: RHS 146A, yellow-green.

*Color of mature phylloclade.*—Upper and lower surfaces: RHS 147A, yellow-green.

*Venation.*—Pattern: Costate. Color: Upper and lower surfaces: RHS 146A, yellow-green.

Areole: Not true areole structure; tip of phylloclade is barbellate, 5 to 12 short hairs or bristles.

Inflorescence description:

*Arrangement and appearance.*—Single, double or triple sessile flowers borne on apical end of phylloclades. Flowers are tubular, hose-in-hose perianth. When flowers are fully open, they form a right angle to the phylloclade. Flowers persistent.

*Natural flowering season.*—Flowering occurs from February to April (northern hemisphere), but can be changed depending on short day photo-treatments.

*Flowering response time.*—About 8 to 9 weeks after short day and vernalization.

*Rate of flowers opening.*—About 1 to 2 per week, depending on temperature and light.

*Flowering longevity* (*dependent on temperature and light conditions*).—About 5 to 6 days.

*Fragrance.*—None.

*Quantity of flowers per lateral branch.*—About 1 to 3.

*Quantity of buds per lateral branch.*—About 2.

*Quantity of flowers and buds per plant.*—About 30 to 45.

*Flower bud.*—Length: Ranging from 0 to 35 mm (before anthesis). Width: Ranging from 0 to 1 cm. Shape: Ovoid to lanceolatoid. Color: RHS N74A, red-purple.

*Flower.*—Type: Single. Shape: Tubular, hose-in-hose triple perianth. Aspect: Upright to vertical during development. Persistent or self-cleaning: Persistent.

*Corolla size.*—Height: About 4 cm to 5 cm (including ovary). Diameter: About 3 cm to 4 cm. Tube length: About 2 cm to 3 cm. Tube diameter: About 10 mm.

*Petals.*—Quantity: Apical Whorl: About 10; Basal whorl: About 5 to 7. Length: About 2.6 cm. Width: About 6 mm to 8 mm. Shape: Oval. Apex: Retuse. Base: Apical Whorl: Fused; Basal Whorl: Free. Margin: Entire. Appearance: Matte. Texture (both surfaces): Silky. Color (When Opening): Upper and lower surfaces: Petals: RHS N74B, red-purple; Tube: RHS N74C, red-purple. Color (When Fully Opened): Upper and lower surfaces: Petals: RHS N74C, red-purple; Tube: RHS N74D, red-purple. Color Fades to: RHS N78A, purple.

*Petaloids.*—Arrangement: Free. Quantity: About 5 to 6. Length: About 10 mm to 20 mm. Width: About 5 mm to 7 mm. Shape: Oval. Apex: Acute. Base: Fused. Margin: Entire. Texture (both surfaces): Silky. Color (mature and immature): RHS N74B, red-purple.

*Sepals.*—Quantity: About 5. Length: About 8 mm to 10 mm. Width: About 1 mm. Shape: Ovate. Apex: Obtuse to rounded. Base: Truncate. Margin: Grooved. Texture (both surfaces): Glabrous, silky. Color (Immature and Mature): RHS 183A, grey-brown.

Reproductive organs:

*Androecium.*—Stamen: Quantity: Many (about 50 to 70), polyandrous, incurved. Some filaments fused to perianth tube (connate). Length: About 15 mm. Color: RHS N74B, red-purple. Anther: Shape: Ovoid. Length: About 1 mm. Color: RHS 17A, yellow-orange. Filament: Length: About 13 to 14 mm. Color: RHS N74B, red-purple. Pollen: Amount: Abundant. Color: RHS 17A, yellow-orange.

*Gynoecium.*—Pistil: Quantity: 1. Shape: Claw-like. Length: About 25 mm. Stigma: Shape: Ovoid. Color: RHS 73D, yellow-white. Style: Length: About 25 mm, slightly curved. Color: RHS N74B, red-purple. Ovary: Shape: Angular. Length: About 4 to 6 mm. Width: About 4 mm. Color: RHS 144B, yellow-green.

Seeds/fruit: None observed.

Disease/pest resistance: No test for disease/pest resistance have been performed yet.

Disease/pest susceptibility: No test for disease/pest resistance have been performed yet.

Temperature tolerance: Tolerant to a low temperature of about 2° C. and to a high temperature about 40° C. Good tolerance to drought.

I claim:

1. A new and distinct *Rhipsalidopsis* plant named '7304G', as illustrated and described herein.

* * * * *